(12) United States Patent
Hilpert

(10) Patent No.: US 9,181,232 B2
(45) Date of Patent: Nov. 10, 2015

(54) DIFLUORO-HEXAHYDRO-CYCLOPENTAOXAZINYLS AND DIFLUORO-HEXAHYDRO-BENZOOXAZINYLS AS BACE1 INHIBITORS

(71) Applicant: Hoffmann-La Roche Inc., Nutley, NJ (US)

(72) Inventor: Hans Hilpert, Muenchenstein (CH)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/406,289

(22) PCT Filed: Jun. 24, 2013

(86) PCT No.: PCT/EP2013/063086
§ 371 (c)(1),
(2) Date: Dec. 8, 2014

(87) PCT Pub. No.: WO2014/001228
PCT Pub. Date: Jan. 3, 2014

(65) Prior Publication Data
US 2015/0133440 A1    May 14, 2015

(30) Foreign Application Priority Data
Jun. 26, 2012    (EP) .................................... 12173690

(51) Int. Cl.
*C07D 413/12* (2006.01)
*C07D 265/12* (2006.01)
*A61K 31/536* (2006.01)

(52) U.S. Cl.
CPC .................................. *C07D 413/12* (2013.01)

(58) Field of Classification Search
CPC ........................... C07D 265/12; A61K 31/536
USPC ......................................... 514/230.5; 544/90
See application file for complete search history.

(56) References Cited

FOREIGN PATENT DOCUMENTS

WO    WO 2011009898 A1 *    1/2011

* cited by examiner

*Primary Examiner* — Kahsay Habte

(57) ABSTRACT

Provided herein is a compound of formula I:

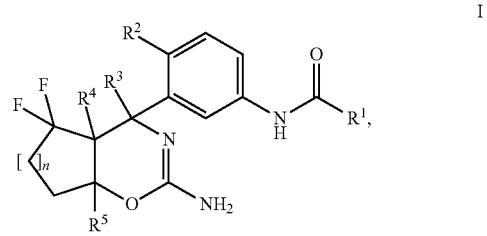

as wells as a pharmaceutical composition, a process of making and a method of using a compound of formula I. The compounds of formula I are BACE1 inhibitors useful for the treatment of, for example, Alzheimer's Disease.

16 Claims, No Drawings

DIFLUORO-HEXAHYDRO-CYCLOPENTAOXAZINYLS AND DIFLUORO-HEXAHYDRO-BENZOOXAZINYLS AS BACE1 INHIBITORS

CROSS-REFERENCE TO RELATED APPLICATIONS

This application is a National Stage Application of PCT/EP2013/063086 filed Jun. 24, 2013, which claims priority from European Patent Application No. 12173690.4, filed on Jun. 26, 2012. The priority of both said PCT and European Patent Application are claimed. Each of prior mentioned applications is hereby incorporated by reference herein in its entirety.

BACKGROUND ART

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al.[1], Selkoe[2]). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space, their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al.[3]). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al.[4], Roberds et al.[5]). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al.[6]). It is thus presumed that inhibitors of BACE1 activity can be useful agents for therapeutic intervention in Alzheimer's Disease (AD). WO 2011071135[7] discloses oxazine derivatives suitable as BACE1 inhibitors.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

Objects of the present invention are novel compounds of formula I, their manufacture, medicaments based on a compound in accordance with the invention and their production as well as the use of compounds of formula I in the control or prevention of illnesses such as Alzheimer's disease. The novel compounds of formula I have improved pharmacological properties such as low ER values.

The present invention provides novel compounds of formula I, which are difluoro-cyclopentaoxazinyls and difluoroenzooxazinyls having BACE1 inhibitory properties, their manufacture, pharmaceutical compositions containing them and their use as therapeutically active substances.

FIELD OF THE INVENTION

The present invention provides a compounds of formula I,

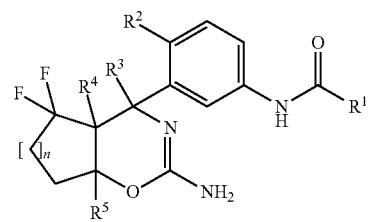

wherein the substituents and variables are as described below and in the claims, or a pharmaceutically acceptable salt thereof.

The present compounds have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or fl-amyloid plaques and further deposits, particularly Alzheimer's disease.

DETAILED DESCRIPTION OF THE INVENTION

Object of the present invention is a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with inhibition of BACE1 activity, such as Alzheimer's disease. Furthermore, the formation, or formation and deposition, of β-amyloid plaques in, on or around neurological tissue (e.g., the brain) are inhibited by the present compounds by inhibiting the AO production from APP or an APP fragment.

The following definitions of the general terms used in the present description apply irrespectively of whether the terms in question appear alone or in combination with other groups.

The term "$C_{1-6}$-alkyl", alone or in combination with other groups, stands for a hydrocarbon radical which may be linear or branched, with single or multiple branching, wherein the alkyl group in general contains 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular "$C_{1-6}$-alkyl" are groups with 1 to 5 carbon atoms. Specific groups are methyl, ethyl and t-butyl. Most specific group is methyl.

The term "cyano-$C_{1-6}$-alkyl", alone or in combination with other groups, refers to $C_{1-6}$-alkyl as defined herein, which is substituted by one or multiple cyano, in particular 1-5 cyano, more particular 1 cyano. Examples are cyano-methyl and the like.

The term "halogen-$C_{1-6}$-alkyl", alone or in combination with other groups, refers to $C_{1-6}$-alkyl as defined herein, which is substituted by one or multiple halogen, in particular 1-5 halogen, more particular 1-3 halogen, most particular 1 halogen or 3 halogen. Particular halogen is fluoro. Examples are difluoromethyl, chloromethyl, fluoromethyl and the like. A specific group is $CH_2F$.

The term "$C_{1-6}$-alkoxy-$C_{1-6}$-alkyl", alone or in combination with other groups, refers to $C_{1-6}$-alkyl, which is substituted by one or multiple $C_{1-6}$-alkoxy as defined herein. Examples are MeO-Me, 1MeO-Et, 2MeO-Et, 1MeO-2EtO-propyl and the like.

The term "cyano", alone or in combination with other groups, refers to N≡C—(NC—).

The term "halogen", alone or in combination with other groups, denotes chloro (Cl), iodo (I), fluoro (F) and bromo (Br). Particular "halogen" is Cl and F.

The term "aryl", alone or in combination with other groups, refers to an aromatic carbocyclic group containing 6 to 14, in particular 6 to 10, carbon atoms and having at least one aromatic ring or multiple condensed rings in which at least one ring is aromatic. Examples of "aryl" include benzyl, biphenyl, indanyl, naphthyl, phenyl (Ph) and the like. Particular "aryl" group is phenyl.

The term "heteroaryl", alone or in combination with other groups, refers to an aromatic carbocyclic group of having a single 4 to 8 membered ring or multiple condensed rings containing 6 to 14, in particular 6 to 10 ring atoms and containing 1, 2 or 3 heteroatoms individually selected from N, O and S, in particular N and O, in which group at least one heterocyclic ring is aromatic. Particular heteroaryl groups have a single 5 or a single 6 membered ring. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" groups are pyridinyl, pyrazinyl and thiophenyl. Specific groups are pyridin-2-yl, pyrazin-2-yl and thiophen-2-yl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (isobutoxy), 2-butoxy (sec-butoxy), t-butoxy (tert-butoxy), isopentyloxy (i-pentyloxy) and the like. Particular "$C_{1-6}$-alkoxy" groups have 1 to 4 carbon atoms. Specific groups are methoxy and ethoxy.

The term "halogen-$C_{1-6}$-alkoxy", alone or in combination with other groups, refers to $C_{1-6}$-alkoxy as defined herein, which is substituted by one or multiple halogens, in particular fluoro. Particular "halogen-$C_{1-6}$-alkoxy" groups are fluoro-$C_{1-6}$-alkoxy.

The term "$C_{2-6}$-alkynyl-$C_{1-6}$-alkoxy", alone or in combination with other groups, refers to $C_{1-6}$-alkoxy as defined herein, which is substituted by one or multiple $C_{2-6}$-alkynyl as defined herein. Particular "$C_{2-6}$-alkynyl-$C_{1-6}$-alkoxy" group is 5-but-2-ynyloxy.

The term "$C_{2-6}$-alkynyl", alone or in combination with other groups, denotes a monovalent linear or branched saturated hydrocarbon group of 2 to 6 carbon atoms, in particular from 2 to 4 carbon atoms, and comprising one, two or three triple bonds. Examples of "$C_{2-6}$-alkynyl" include ethynyl and propynyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular acids are formic acid, trifluoroacetic acid and hydrochloric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. In particular it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The IC$_{50}$ value can be converted to an absolute inhibition constant (Ki) using the Cheng-Prusoff equation[8]. The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (–log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as in particular, more particular and most particular definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The blood-brain barrier is an impediment to the entry of therapeutic substances into the brain. P-glycoprotein (P-gp) is efflux transporters in many tissues including the intestine, brain and kidney. Since P-glycoprotein can actively transport therapeutic substances out of the cell, it is regarded responsible for the penetration of certain therapeutic substances into the brain. The efflux ratio (ER) is a highly sensitive parameter that can be used for the degree of P-gp inhibition.

The term "aromatic" denotes the conventional idea of aromaticity as defined in the literature, in particular in IUPAC[9].

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure.

The invention also provides pharmaceutical compositions, methods of using, and methods of preparing the aforementioned compounds.

All separate embodiments may be combined.

One embodiment of the invention is a compound of formula I,

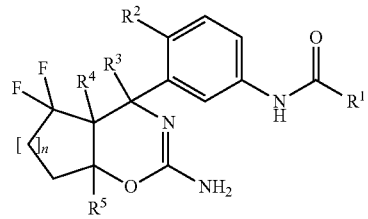

wherein
R$^1$ is selected from the group consisting of
  i) aryl,
  ii) aryl substituted by 1-4 substituents individually selected from cyano, cyano-C$_{1-6}$-alkyl, halogen, halogen-C$_{1-6}$-alkoxy, halogen-C$_{1-6}$-alkyl, C$_{1-6}$-alkoxy, C$_{1-6}$-alkoxy-C$_{1-6}$-alkyl, C$_{2-6}$-alkynyl-C$_{1-6}$-alkoxy, C$_{2-6}$-alkynyl and C$_{1-6}$-alkyl,
  iii) heteroaryl, and
  iv) heteroaryl substituted by 1-4 substituents individually selected from cyano, cyano-C$_{1-6}$-alkyl, halogen, halogen-C$_{1-6}$-alkoxy, halogen-C$_{1-6}$-alkyl, C$_{1-6}$-alkoxy, C$_{1-6}$-alkoxy-C$_{1-6}$-alkyl, C$_{2-6}$-alkynyl-C$_{1-6}$-alkoxy, C$_{2-6}$-alkynyl and C$_{1-6}$-alkyl;
R$^2$ is selected from the group consisting of
  i) hydrogen,
  ii) C$_{1-6}$-alkyl, and
  iii) halogen;
R$^3$ is selected from the group consisting of
  i) C$_{1-6}$-alkyl, and
  ii) halogen-C$_{1-6}$-alkyl;
R$^4$ is selected from the group consisting of
  i) hydrogen, and
  ii) C$_{1-6}$-alkyl, and
R$^5$ is selected from the group consisting of
  i) hydrogen, and
  ii) C$_{1-6}$-alkyl;
n is 1 or 2;
or pharmaceutically acceptable salts thereof.

A certain embodiment of the invention provides a compound of formula I, which is of formula Ia.

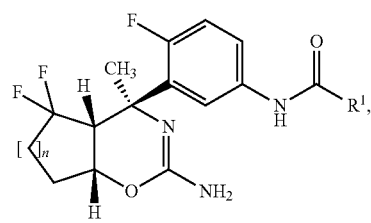

wherein n and R$^1$ are as described herein.

A certain embodiment of the invention provides a compound of formula I as described herein, wherein R$^1$ is heteroaryl substituted by 1-2 substituents individually selected from cyano, halogen, halogen-C$_{1-6}$-alkyl and C$_{2-6}$-alkynyl-C$_{1-6}$-alkoxy.

A certain embodiment of the invention provides a compound of formula I as described herein, wherein R$^1$ is selected from
  i) pyridinyl substituted by 1-2 substituents individually selected from cyano and halogen, ii) pyrazinyl substituted by 1-2 substituents individually selected from cyano, halogen-$C_{1-6}$-alkyl and $C_{2-6}$-alkynyl-$C_{1-6}$-alkoxy, and iii) thiophenyl substituted by 1-2 halogen.

A certain embodiment of the invention provides a compound of formula I as described herein, wherein $R^1$ is pyridinyl substituted by 1-2 substituents individually selected from cyano and halogen.

A certain embodiment of the invention provides a compound of formula I as described herein, wherein $R^1$ is pyrazinyl substituted by 1-2 substituents individually selected from cyano, halogen-$C_{1-6}$-alkyl and $C_{2-6}$-alkynyl-$C_{1-6}$-alkoxy.

A certain embodiment of the invention provides a compound of formula I as described herein, wherein $R^1$ is thiophenyl substituted by 1-2 halogen.

A certain embodiment of the invention provides a compound of formula I as described herein, wherein $R^1$ is 5-but-2-ynyloxy-pyrazin-2-yl, 5-cyano-pyridin-2-yl, 5-chloro-pyridin-2-yl, 5-fluoromethyl-pyrazin-2-yl, 5-cyano-pyrazin-2-yl, 5-chloro-pyridin-2-yl, 5-cyano-pyridin-2-yl, 5-chloro-thiophen-2-yl or 5-(1,1-difluoro-ethyl)-pyrazin-2-yl.

A certain embodiment of the invention provides a compound of formula I as described herein, wherein $R^1$ is 5-but-2-ynyloxy-pyrazin-2-yl.

A certain embodiment of the invention provides a compound of formula I as described herein, wherein $R^1$ is 5-cyano-pyridin-2-yl.

A certain embodiment of the invention provides a compound of formula I as described herein, wherein $R^1$ is 5-chloro-pyridin-2-yl.

A certain embodiment of the invention provides a compound of formula I as described herein, wherein $R^1$ is 5-fluoromethyl-pyrazin-2-yl.

A certain embodiment of the invention provides a compound of formula I as described herein, wherein $R^1$ is 5-cyano-pyrazin-2-yl.

A certain embodiment of the invention provides a compound of formula I as described herein, wherein $R^1$ is 5-chloro-pyridin-2-yl.

A certain embodiment of the invention provides a compound of formula I as described herein, wherein $R^1$ is 5-cyano-pyridin-2-yl.

A certain embodiment of the invention provides a compound of formula I as described herein, wherein $R^1$ is 5-chloro-thiophen-2-yl.

A certain embodiment of the invention provides a compound of formula I as described herein, wherein $R^1$ is 5-(1,1-difluoro-ethyl)-pyrazin-2-yl.

A certain embodiment of the invention provides a compound of formula I as described herein, wherein $R^2$ is halogen.

A certain embodiment of the invention provides a compound of formula I as described herein, wherein $R^2$ is F.

A certain embodiment of the invention provides a compound of formula I as described herein, wherein $R^3$ is $C_{1-6}$-alkyl.

A certain embodiment of the invention provides a compound of formula I as described herein, wherein $R^3$ is methyl.

A certain embodiment of the invention provides a compound of formula I as described herein, wherein $R^4$ is hydrogen.

A certain embodiment of the invention provides a compound of formula I as described herein, wherein $R^5$ is hydrogen.

A certain embodiment of the invention provides a compound of formula I as described herein, wherein n is 1.

A certain embodiment of the invention provides a compound of formula I as described herein, wherein n is 2.

A certain embodiment of the invention provides a compound of formula I as described herein, selected from the group consisting of 5-But-2-ynyloxy-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-henyl]-amide, 5-Fluoromethyl-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide, 5-Cyano-pyridine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide, 5-Chloro-pyridine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide, 5-Cyano-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl-amide, 5-Chloro-pyridine-2-carboxylic acid [3-((4S,4aR,8aR)-2-amino-5,5-difluoro-4-methyl-4a,5,6,7,8,8a-hexahydro-4H-benzo[e][1,3]oxazin-4-yl)-4-fluoro-phenyl]-amide, 5-Cyano-pyridine-2-carboxylic acid [3-((4S,4aR,8aR)-2-amino-5,5-difluoro-4-methyl-4a,5,6,7,8,8a-hexahydro-4H-benzo[e][1,3]oxazin-4-yl)-4-fluoro-phenyl]-amide, 5-Chloro-thiophene-2-carboxylic acid [3-((4S,4aR,8aR)-2-amino-5,5-difluoro-4-methyl-4a,5,6,7,8,8a-hexahydro-4H-benzo[e][1,3]oxazin-4-yl)-4-fluoro-phenyl]-amide, and 5-(1,1-Difluoro-ethyl)-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide, or a pharmaceutical acceptable salt thereof.

A certain embodiment of the invention provides a compound of formula I as described herein, which is 5-But-2-ynyloxy-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-henyl]-amide.

A certain embodiment of the invention provides a compound of formula I as described herein, which is 5-Fluoromethyl-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Cyano-pyridine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Chloro-pyridine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Cyano-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl-amide.

A certain embodiment of the invention provides a compound of formula I as described herein, which is 5-Chloro-pyridine-2-carboxylic acid [3-((4S,4aR,8aR)-2-amino-5,5-difluoro-4-methyl-4a,5,6,7,8,8a-hexahydro-4H-benzo[e][1,3]oxazin-4-yl)-4-fluoro-phenyl]-amide.

A certain embodiment of the invention provides a compound of formula I as described herein, which is 5-Cyano-pyridine-2-carboxylic acid [3-((4S,4aR,8aR)-2-amino-5,5-difluoro-4-methyl-4a,5,6,7,8,8a-hexahydro-4H-benzo[e][1,3]oxazin-4-yl)-4-fluoro-phenyl]-amide.

A certain embodiment of the invention provides a compound of formula I as described herein, which is 5-Chloro-thiophene-2-carboxylic acid [3-((4S,4aR,8aR)-2-amino-5,5-difluoro-4-methyl-4a,5,6,7,8,8a-hexahydro-4H-benzo[e][1,3]oxazin-4-yl)-4-fluoro-phenyl]-amide.

A certain embodiment of the invention provides a compound of formula I as described herein, which is 5-(1,1-Difluoro-ethyl)-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide.

A certain embodiment of the invention provides a process to synthesize a compound of formula I as described herein, which process comprises reacting a compound of formula I' with a compound of formula XIV.

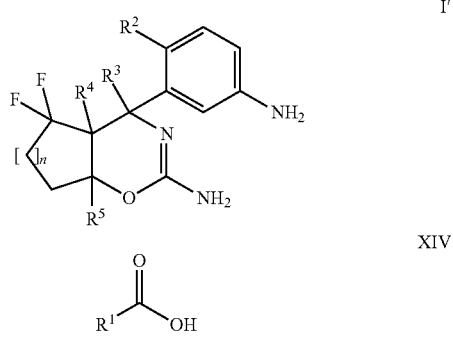

wherein n, $R^1$, $R^2$, $R^3$, $R^4$, $R^5$ are as described herein.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides a compound of formula I as described herein for the use in inhibition of BACE1 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides a compound of formula I as described herein for the use in the therapeutic and/or prophylactic treatment of Alzheimer's disease.

A certain embodiment of the invention provides a method for the use in inhibition of BACE1 activity, particularly for the therapeutic and/or prophylactic treatment of diseases and disorders characterized by elevated β-amyloid levels and/or β-amyloid oligomers and/or β-amyloid plaques and further deposits or Alzheimer's disease, which method comprises administering compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates.

The skilled person in the art will recognize that the compounds of formula I can exist in tautomeric forms, e.g. in the following tautomeric form:

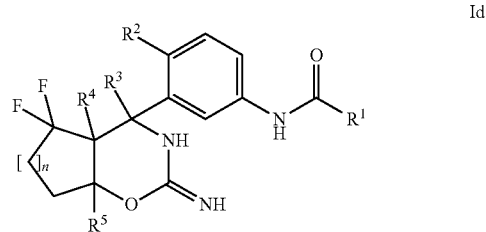

All tautomeric forms are encompassed in the present invention.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric centre of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Certain examples of isomers of a compound of formula I is a compound of formula Ib or a compound of formula Ic, wherein the residues have the meaning as described in any of the embodiments, in particular a compound of formula Ic.

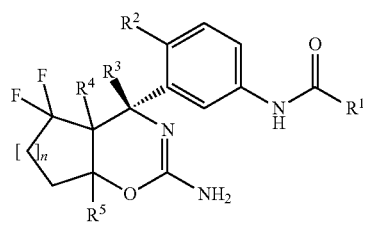

Ib

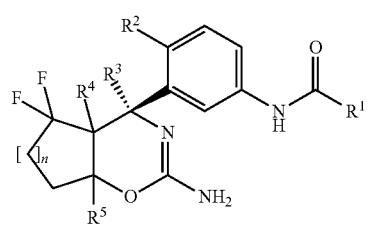

Ic

In the embodiments, where optically pure enantiomers are provided, optically pure enantiomer means that the compound contains >90% of the desired isomer by weight, in particular >95% of the desired isomer by weight, or more particular >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I may be prepared in accordance with the following schemes. The starting material is commercially available or may be prepared in accordance with known methods. Any previously defined residues and variables will continue to have the previously defined meaning unless otherwise indicated.

Compounds of general formula IV are prepared by reaction of a nitro compound of formula II with α,β-unsaturated ketones of general formula III in the presence of an activating reagent such as e.g. an isocyanate, in particular phenylisocyanate, and a catalytic amount of a base, in particular an alkyl amine, more particular triethylamine, in a solvent such as benzene or toluene, in particular benzene, or an alkyl ether, in particular diethyl ether, to give the dihydroisoxazole of general formula IV.

Fluorination of the dihydroisoxazoles of general formula IV to give the difluoro-dihydroisoxazoles of general formula VI is performed in the presence of a fluorinating agent, in particular morpholinosulfur trifluoride (V), in an inert solvent, in particular dichloromethane.

Isoxazolidines of general formula VIII are prepared by reacting an arylhalogenide, in particular an arylbromide, like e.g. arylbromide VII, with an alkyl lithium reagent, in particular n-butyllithium, to give an aryllithium species, which can be reacted with dihydroisoxazoles of general formula VI in the presence of a Lewis acid, in particular boron trifluoride etherate, in a solvent mixture consisting of an ether, in particular tetrahydrofuran and toluene, at −100° C. to −20° C., in particular at −78° C.

The resolution of racemic isoxazolidines of general formula VIII to give the chiral isoxazolidines of general formula IXa and IXb can be achieved by high-performance liquid chromatography (HPLC) on a chiral phase like e.g. on a Chiralpak AD column using a mixture of n-heptane and ethanol as the eluent.

The hydrogenolysis of the chiral isoxazolidines of general formula IX to the aminoalcohols of general formula X can be accomplished best by transfer hydrogenolysis using palladium as the catalyst, in particular palladium on carbon, and a hydrogen source, e.g. a salt of formic acid, in particular ammonium formate, in a protic solvent such as an alcohol, in particular ethanol.

Oxazines of general formula XI can be prepared by reaction of aminoalcohols of general formula X with cyanogen bromide in a solvent such as an alcohol, in particular ethanol, at elevated temperature. Alternatively, the reaction can be carried out in two step sequence using cyanogen bromide and a buffer such as e.g. sodium acetate in the presence of a solvent such as e.g. acetonitrile followed by cyclisation of the intermediate in the presence of a mineral acid, in particular hydrochloric acid, in a solvent such as an ether, in particular 1,4-dioxane.

The nitration of oxazines of general formula XI to give nitro-oxazines of general formula XII follows a standard procedure involving neat sulfuric acid and fuming nitric acid without using a solvent.

The reduction of the nitro group in intermediates of general formula XII can be accomplished by hydrogenation using a catalyst such as palladium on carbon in protic solvents, such as alcohols, in particular ethanol or methanol, to yield the anilines of general formula XIII.

Selective amide coupling of anilines of general formula XIII and carboxylic acids of general formula XIV to give amides of general formula Ia' can be effected with 4-(4,6-dimethoxy[1.3.5]triazin-2-yl)-4-methylmorpholinium chloride (DMTMM) hydrate in a solvent such as an alcohol, in particular methanol.

Scheme 1: Synthesis of compounds of formula Ia'

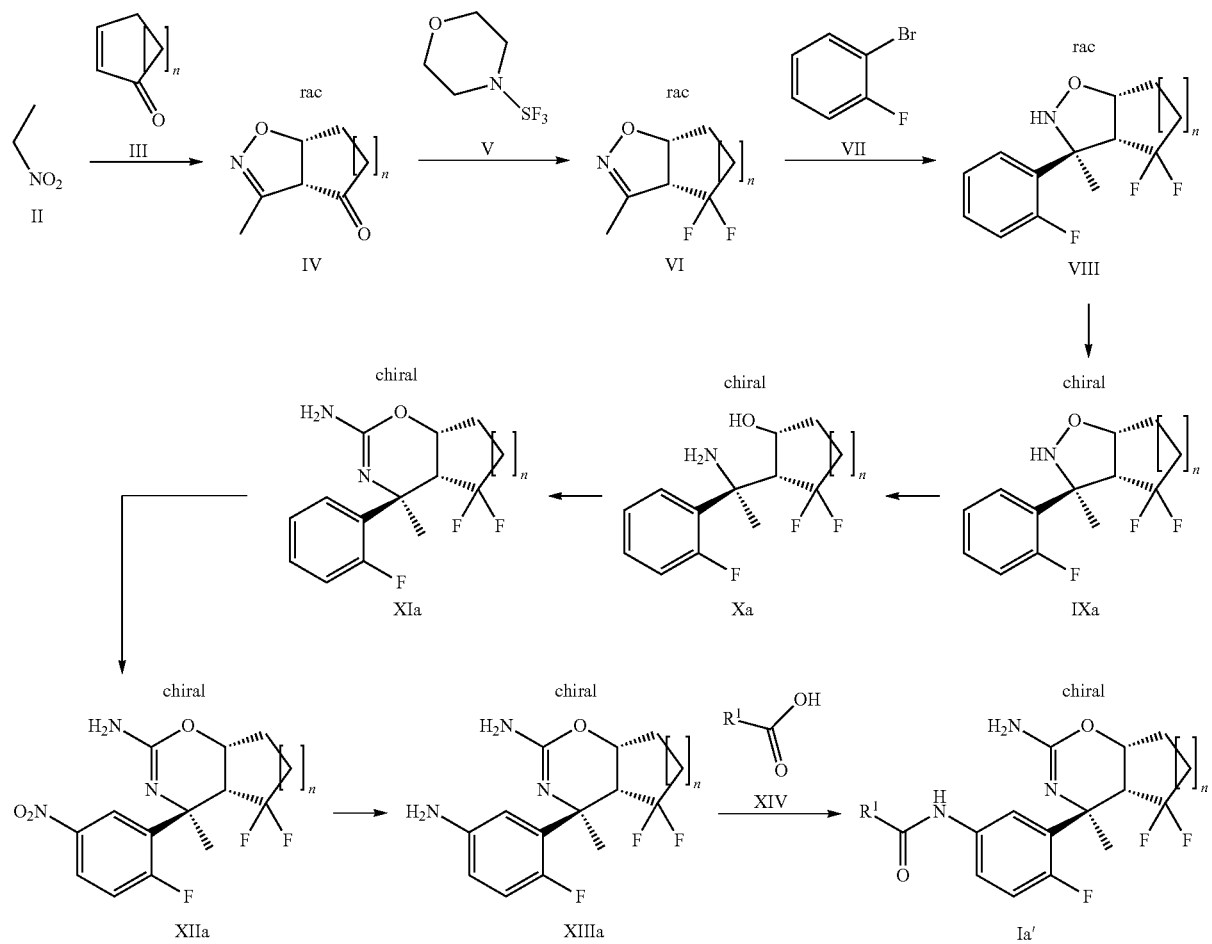

The corresponding pharmaceutically acceptable salts with acids can be obtained by standard methods known to the person skilled in the art, e.g. by dissolving the compound of formula I in a suitable solvent such as e.g. dioxane or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula I as well as all intermediate products can be prepared according to analogous methods or according to the methods set forth herewithin. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The compounds of formula I and their pharmaceutically acceptable salts possess valuable pharmacological properties. It has been found that the compounds of the present invention are associated with inhibition of BACE1 activity. The compounds were investigated in accordance with the test given hereinafter.

Cellular Aβ-Lowering Assay:

Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96 well ELISA plates (e.g., Nunc MaxiSorb) were coated with monoclonal antibody which specifically recognize the C-terminal end of Aβ40[10]. After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/$H_2O_2$ in citric acid buffer. After stopping the reaction with one volume 1 N $H_2SO_4$ the reaction was measured in an ELISA reader at 450 nm wavelength. The concentrations of Aβ in the culture supernatants were calculated from a standard curve obtained with known amounts of pure Aβ peptide.

TABLE 1

IC$_{50}$ values of selected examples

| Exam. | Structure | BACE1 cell act. Aβ40 IC$_{50}$ [μM] |
|---|---|---|
| 1 | 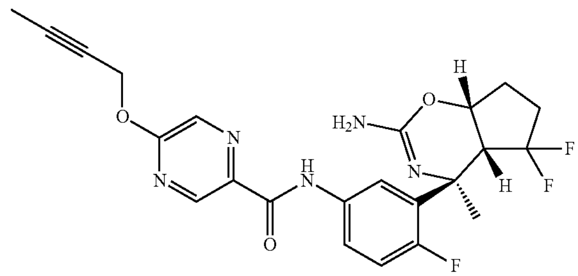 [SMILES: CC#CCOc1cnc(C(=O)Nc2ccc(F)c([C@@]3(C)N=C(N)O[C@@H]4CCC(F)(F)[C@@H]43)c2)cn1] | 0.0004 |
| 2 | 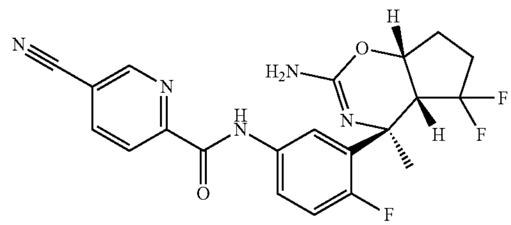 [SMILES: C[C@]1(c2cc(NC(=O)c3ccc(C#N)cn3)ccc2F)N=C(N)O[C@@H]2CCC(F)(F)[C@@H]21] | 0.0015 |
| 3 | 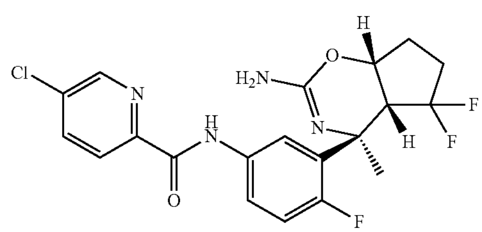 [SMILES: C[C@]1(c2cc(NC(=O)c3ccc(Cl)cn3)ccc2F)N=C(N)O[C@@H]2CCC(F)(F)[C@@H]21] | 0.0019 |
| 4 | 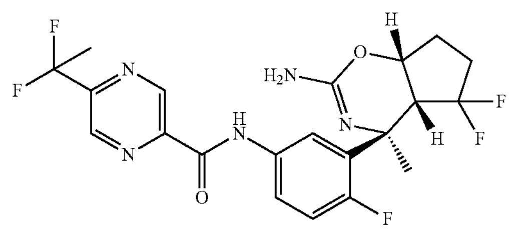 [SMILES: CC(F)(F)c1cnc(C(=O)Nc2ccc(F)c([C@@]3(C)N=C(N)O[C@@H]4CCC(F)(F)[C@@H]43)c2)cn1] | 0.0089 |
| 5 | 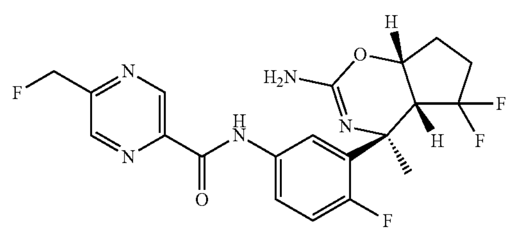 [SMILES: C[C@]1(c2cc(NC(=O)c3cnc(CF)cn3)ccc2F)N=C(N)O[C@@H]2CCC(F)(F)[C@@H]21] | 0.0051 |

TABLE 1-continued

IC$_{50}$ values of selected examples

| Exam. | Structure | BACE1 cell act. Aβ40 IC$_{50}$ [μM] |
|---|---|---|
| 6 | 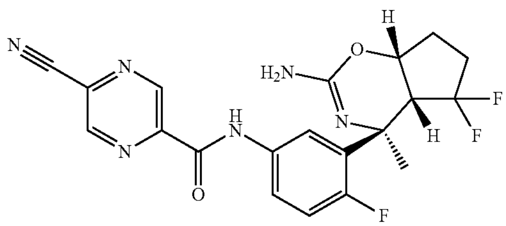 [SMILES: C[C@]1(c2cc(NC(=O)c3cnc(C#N)cn3)ccc2F)N=C(N)O[C@@H]2CCC(F)(F)[C@@H]21] | 0.0055 |
| 7 | 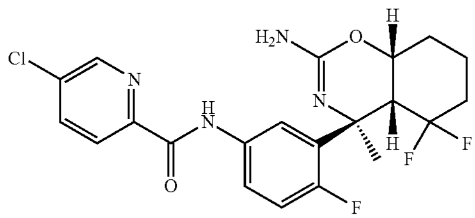 [SMILES: C[C@]1(c2cc(NC(=O)c3ccc(Cl)cn3)ccc2F)N=C(N)O[C@@H]2CCCC(F)(F)[C@@H]21] | 0.0049 |
| 8 | 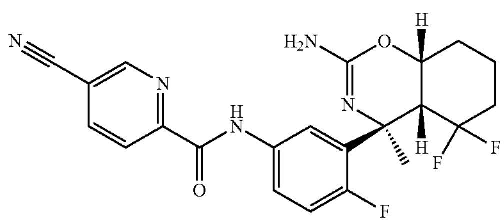 [SMILES: C[C@]1(c2cc(NC(=O)c3ccc(C#N)cn3)ccc2F)N=C(N)O[C@@H]2CCCC(F)(F)[C@@H]21] | 0.0022 |
| 9 | 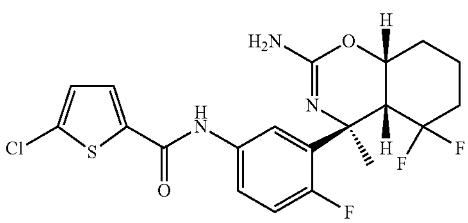 [SMILES: C[C@]1(c2cc(NC(=O)c3ccc(Cl)s3)ccc2F)N=C(N)O[C@@H]2CCCC(F)(F)[C@@H]21] | 0.350 |

P-gp (P-Glycoprotein) Assay

Cell Lines Used for Transport Experiments

The LLC-PK1 cell line (ATCC #CL-101) is a porcine kidney epithelial cell line. The MDR1 (Human multidrug resistance protein 1) transfected cell lines were obtained from Dr. A. Schinkel, The Netherlands Cancer Institute (Amsterdam, The Netherlands). All cell lines were cultured on permeable inserts (96-insert plates Millipore, 0.11 cm$^2$ area, pore size 0.4 μm) at 0.73*10$^6$ cells/ml. Transport measurements were performed at day 4 after seeding. Tightness of the cell monolayer was controlled via the permeability of the extra-cellular marker lucifer yellow (10 μM). Experiments showing lucifer yellow permeation superior to 25 nm/s were rejected.

In Vitro Transport Experiments

Bidirectional transcellular transport using LLC-PK1 and L-MDR1 LLC-PK1 cells exogenously expressing the human MDR1)

The experiments were performed on a TECAN automated liquid handling system. Briefly, medium was removed from all compartments and the medium of receiver side was replaced with culture medium. The trans-cellular transport measurements were initiated by adding the substrate together with extracellular marker lucifer yellow to the donor side. Inhibitors were added to both sides (1 μM elacridar). Transport experiments were performed both in the basolateral-to-apical and apical-to-basolateral directions with 3 wells each. The plates were incubated at 37° C. and 5% CO$_2$ in a Liconic incubator. Samples were taken from the donor and the opposite (acceptor) side after 2 hours incubation. Concentrations of substrate in both compartments were determined by scintillation counting (digoxin) or by LC-MS/MS. The extracellular marker (lucifer yellow) was quantified using a spectrafluor plus reader at 430/535 nm (Ex/Em). In each experiment 3 different inserts were used for each condition and a mean was calculated.

Data Analysis

Bidirectional Transcellular Transport Using LLC-PK1 and L-MDR1 Cells

For the transcellular transport, the following equation was used for data evaluation:

$$P_{app} = \frac{1}{A * C_0} * \frac{dQ}{dt}$$

Where $P_{app}$, A, $C_0$, and dQ/dt represent the apparent permeability, the filter surface area, the initial concentration, and the amount transported per time period, respectively. $P_{app}$ values were calculated on the basis of a single time point (2 h).

Transport efflux ratios (ER) were calculated as follows:

$$ER = \frac{P_{app}BA}{P_{app}AB}$$

Where $P_{app}BA$ is the permeability value in the basolateral-to-apical direction, and $P_{app}AB$ the permeability value in the apical-to-basolateral direction. $P_{app}$ were not corrected for flux of the extracellular marker lucifer yellow, which was used to assess the quality of the cell monolayers.

CYP Inhibition Assay

Inhibition of cytochromes P450 (CYPs) 2C9, 2D6 and 3A4 was assessed using human liver microsomes and CYP-selective substrate metabolism reactions. 50 µl incubations were made up containing (finally) 0.2 mg/ml pooled human liver microsomes, 5 µM substrate (diclofenac for CYP2C9 [4'hydroxylase], dextromethorphan for CYP2D6 [O-demethylase] or midazolam for CYP3A4 [1'hydroxylase]), 0.25 µL DMSO containing test inhibitor and NADPH regenerating system. Test inhibitor concentrations of 50, 16.7, 5.6, 1.9, 0.6 and 0.2 µM were assessed in singlicate. Incubations were prewarmed to 37° C. for 10 minutes before initiation by addition of NADPH regenerating system. Incubations were quenched after 5 minutes (20 minutes for dextromethorphan) by addition of 50 µl cold acetonitrile containing 20 ng/ml 4-OH-diclofenac-13C6, 20 ng/mL dextrorphan-D3 and 20 ng/mL 1-OH-midazolam-D4. Quenched incubates were stored at −20° C. for at least 1 hour before centrifugation (20,000×g, 20 minutes). Supernatants were removed and diluted 1:1 with water prior to analysis using a RapidFire sample injector system and API4000 mass spectrometer. Peak areas for substrate, metabolite and stable-labelled metabolite standard were determined using MS/MS. The peak area ratios between the metabolite generated by the enzymatic reaction and the internal standard were used in subsequent calculations. The percentage of (DMSO) control activity was calculated for each incubate and $IC_{50}$ values estimated by non-linear regression. Sulfaphenazole, quinidine or ketoconazole were tested in each CYP2C9, CYP2D6 or CYP3A4 inhibition experiment, respectively, to ensure assay sensitivity and reproducibility. (Validated assays for human cytochrome P450 activities[11])

PatchXpress hERG Inhibition Assay

The detailed method to quantify hERG channel inhibition by the automated patch clamp system PatchXpress® 7000A (Molecular Devices, Sunnyvale, Calif.) has been described by Guo et al.[12] In brief, Chinese hamster ovary (CHO) cells transfected with the human ether-a-go-go-related gene (hERG) was cultured in Ex-cell 302 media supplemented with 10% fetal bovine serum, 2 mM glutamine and 0.25 mg/ml geneticin and maintained in a $CO_2$ incubator at 37° C. For patch clamp electrophysiology, the external buffer contained (in mM): 150 NaCl, 10 Hepes, 4 KCl, 1.2 $CaCl_2$, 1 $MgCl_2$, pH 7.4 adjusted with HCl and the internal recording solution contained (in mM): 140 KCl, 6 EGTA, 5 Hepes, $MgCl_2$, 5 ATP-$Na_2$, pH 7.2 adjusted with KOH. Once the cell was loaded in the recording chamber and formed a giga ohm seal with the planar glass electrodes (Sealchip™), a whole-cell configuration was achieved by rupturing the cell membrane. The membrane potential was then clamped at −80 mV and the hERG channel activated by a 1-second depolarizing pulse delivered at 0.1 Hz, the hERG current was measured during the 500 ms-repolarizing pulse to −40 mV. After an acceptable hERG current recording was obtained, the cell was first exposed to 0.3% DMSO as the vehicle control, followed by the test article in three ascending, full-log interval concentrations and finally E-4031 at 1 µM (as the positive control) to block the hERG current completely. Each test article was tested on three or more cells and at concentrations up to 30 µM or the solubility limit determined the BD Gentest™ solubility scanner. The inhibition of hERG current at each concentration was normalized to that recorded in the vehicle control, and fitted with Hill equation to calculate $IC_{20}$ and/or $IC_{50}$.

Cathepsin D and Cathepsin E Fluorescent Substrate Kinetic Assays

General Assay Principle

The MR121 fluorescence assays described below are based on the fact that MR121 forms a non-fluorescent ground state complex with tryptophan. In solution this formation occurs at millimolar concentrations of tryptophan. The mechanism can be used to design a generic biochemical assay for proteases. A substrate peptide is labeled at the N-terminus with tryptophan and at the C-terminus with the fluorophore MR121 (for cathepsin D the 10 amino acid peptide WTSVLMAAPC-MR121 was used; for cathepsin E, MR121-CKLVFFAEDW was used). In absence of protease activity, the substrates remain intact and the MR121 fluorescence is reduced by the high local Trp-concentration. If the substrates are cleaved by the enzymes the MR121 fluorescence is recovered.

Assay Procedure

The fluorescent substrate cathepsin D and cathepsin E kinetic assays were performed at room temperature in 384-well microtiter plates (black with clear flat bottom, non binding surface plates from Corning) in a final volume of 51 µl. The test compounds were serially diluted in DMSO (15 concentrations, 1/3 dilution steps) and 1 µl of diluted compounds were mixed for 10 min with 40 µl of cathepsin D (from human liver, Calbiochem) diluted in assay buffer (100 mM sodium acetate, 0.05% BSA, pH 5.5; final concentration: 200 nM) or with 40 µl of recombinant human cathepsin E (R&D Systems) diluted in assay buffer (100 mM sodium acetate, 0.05% BSA, pH 4.5; final concentration: 0.01 nM). After addition of 10 µl of the cathepsin D substrate WTSVLMAAPC-MR121 diluted in cathepsin D assay buffer (final concentration: 300 nM) or 1 of 10 the cathepsin E substrate MR121-CKLVF-FAEDW diluted in cathepsin E assay buffer (final concentration: 300 nM), the plates were strongly shaken for 2 minutes. The enzymatic reaction was followed in a plate: vision reader (Perkin Elmer) (excitation wavelength: 630 nm; emission:

695 nm) for at least 30 minutes in a kinetic measurement detecting an increase of MR121 fluorescence during the reaction time. The slope in the linear range of the kinetic was calculated and the $IC_{50}$ of the test compounds were determined using a four parameter equation for curve fitting.

Detection of Glutathione Conjugates

The assay conditions for the detection of glutathione conjugates follow the procedure described by C. M. Dieckhaus et al.[13]

Results

TABLE 2

Biological data of selected examples

| Ex. | P-gp human [1] | GSH human [2] | hERG [3] | in vivo effect [4] | Cathepsin E $IC_{50}$ [μM] | Cathepsin D $IC_{50}$ [μM] | CYP $IC_{50}$ [μM] [5] | | |
|-----|---------|---------|--------|--------|------------|------------|-----|-----|-----|
|     |         |         |        |        |            |            | 3A4 | 2D6 | 2C9 |
| 1 | B | — | A | A | 97 | 135 | A | B | A |
| 2 | B | NF | A | A | 90 | >200 | A | A | A |
| 4 | — | — | — | — | >200 | 183 | — | — | — |
| 8 | — | NF | A | A | >200 | >200 | A | A | A |
| 9 | — | — | — | — | >200 | 105 | A | B | B |

[1] Efflux ratio: substrate category: A = no or weak substrate (ER < 3); B = good substrate (3 < ER < 10);
[2] NF = in vitro no significant adduct formation relative to control;
[3] A = less than 50% inhibition @ 1 μM;
[4] A = less than 50% of control @ 30 mg/kg p.o.;
[5] A = $IC_{50}$ >10 μM ; B = 1 μM < $IC_{50}$ < 10 μM.

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, in particular 1-100 mg, of a compound of formula I. Examples of compositions according to the invention are:

EXAMPLE A

Tablets of the following composition are manufactured in the usual manner:

TABLE 3 possible tablet composition

| ingredient | mg/tablet | | | |
|---|---|---|---|---|
|   | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.

2. Dry the granules at 50° C.

3. Pass the granules through suitable milling equipment.

4. Add ingredient 5 and mix for three minutes; compress on a suitable press.

EXAMPLE B-1

Capsules of the following composition are manufactured:

TABLE 4 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatine capsules.

EXAMPLE B-2

Soft Gelatine Capsules of the following composition are manufactured:

TABLE 5 possible soft gelatine capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 6 possible soft gelatine capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 7 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

EXAMPLE D

Injection solutions of the following composition are manufactured:

TABLE 8 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 9 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

Synthesis of the intermediate dihydroisoxazoles IV

Intermediate IV-1: rac-(3aR,6aR)-3-Methyl-3a,5,6,6a-tetrahydro-cyclopenta[d]isoxazol-4-one

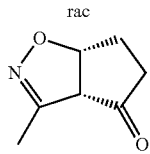

Under an inert atmosphere a solution of nitroethane (4.66 g, 4.44 ml, 62.1 mmol) in ether (15 ml) was treated at room temperature with a solution of cyclopent-2-enone (5 g, 5.1 ml, 60.9 mmol) in ether (90 ml) followed by the addition of triethylamine (70.8 mg, 97.6 µl, 700 µmol) and the dropwise addition of phenyl isocyanate (14.8 g, 13.6 ml, 124 mmol). The light yellow solution was stirred at 25° C. during the weekend. For the workup, the off-white suspension was filtered and washed three times with ether. The filtrate was evaporated, then the crude product was triturated in dichloromethane (15 ml), the solid was filtered off and washed with dichloromethane. After evaporation of the orange-colored filtrate the crude product was purified by flash chromatography on silica gel using a gradient of heptane and ethyl acetate=2:1 to 1:2 as the eluent. The rac-(3aR,6aR)-3-methyl-3a,5,6,6a-tetrahydro-cyclopenta[d]isoxazol-4-one (5.95 g, 70% yield) was obtained as yellow liquid. MS: m/z=139 [M]⁺. In addition, the rac-(3aR,6aS)-3-methyl-3a,4,5,6a-tetrahydro-cyclopenta[d]isoxazol-6-one (0.37 g, 4.3% yield) was obtained as a yellow oil. MS: m/z=139 [M]⁺.

Intermediate IV-2: rac-(3aR,7aR)-3-Methyl-5,6,7,7a-tetrahydro-3aH-benzo[d]isoxazol-4-one

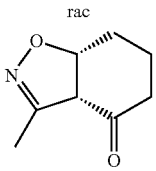

Under an inert atmosphere a solution of nitroethane (5.36 g, 5.1 ml, 71.4 mmol) in ether (20 ml) was treated at room temperature with a solution of cyclohex-2-enone (6.73 g, 6.78 ml, 70 mmol) in ether (120 ml) followed by the addition of triethylamine (70.8 mg, 97.6 µl, 700 µmol) and the dropwise addition (appr. 1 minute) of phenyl isocyanate (17.0 g, 15.6 ml, 143 mmol). The clear solution was stirred at 25° C. for 48 hours while solid started to precipitate after 2 hours. For the workup, the solid material was filtered and washed three times with ether. The yellow filtrate was evaporated, then the yellow crude product was suspended in dichloromethane (30 ml), the solid was filtered off and washed three times with dichloromethane. After evaporation of the filtrate the crude product was purified by flash chromatography on silica gel using a gradient of heptane and ethyl acetate=5:1 to 4:1 to 1:1 as the eluent. The rac-(3aR,7aR)-3-methyl-5,6,7,7a-tetrahydrobenzo[d]isoxazol-4(3aH)-one (7.27 g, 68% yield) was obtained as an orange liquid. MS: m/z=154.1 [M+H]⁺. In addition, the rac-(3aR,7aS)-3-methyl-3a,5,6,7a-tetrahydro-4H-benzo[d]isoxazol-7-one (0.52 g, 4.9% yield) was obtained as a light brown solid. MS: m/z=154.1 [M+H]⁺.

General Procedure B: Synthesis of the Intermediate Dihydroisoxazoles VI

Under an inert atmosphere a solution of the dihydroisoxazole of formula IV (12.2 mmol) in dichloromethane (17 ml) was treated dropwise at 0° C. with morpholinosulfur trifluoride V (26.9 mmol). The solution was allowed to warm to room temperature and stirred for 15 hours. For the workup, the mixture was cooled to 0° C. and quenched with a saturated solution of sodium bicarbonate while keeping the temperature below 20° C. After stirring for 30 minutes the aqueous layer was extracted three times with dichloromethane. The combined organic layers were washed with brine, dried over sodium sulphate and evaporated. The crude product was purified by bulb-to-bulb distillation and flash chromatography on silica gel using mixtures of heptane and ethyl acetate as the eluent to afford the pure dihydroisoxazoles VI.

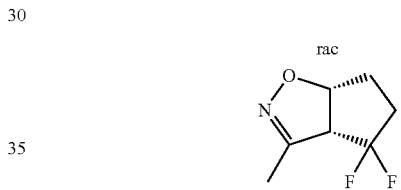

Intermediate VI-1: Starting from rac-(3aR,6aR)-3-methyl-3a,5,6,6a-tetrahydro-cyclopenta[d]isoxazol-4-one (intermediate IV-1), the product rac-(3aR,6aR)-4,4-difluoro-3-methyl-4,5,6,6a-tetrahydro-3aH-cyclopenta[d]isoxazole was obtained as a light yellow liquid (73% yield). MS: m/z=162.2 [M+H]⁺.

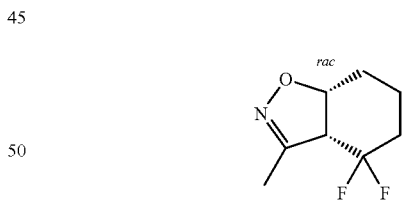

Intermediate VI-2: Starting from rac-(3aR,7aR)-3-methyl-5,6,7,7a-tetrahydro-3aH-benzo[d]isoxazol-4-one (intermediate IV-2), the product rac-(3 aR,7aR)-4,4-difluoro-3-methyl-3a,4,5,6,7,7a-hexahydro-benzo[d]isoxazole was obtained as a 1:1-mixture with rac-(3aR,7aR)-4-fluoro-3-methyl-3a,6,7,7a-tetrahydro-benzo[d]isoxazole as a colorless liquid which was engaged in the step without further purification. MS: m/z=176.2 [M+H]⁺ and MS: m/z=156.2 [M+H]⁺.

General Procedure C: Synthesis of the Intermediate Isoxazolidines VIII and IX

Under an inert atmosphere a solution of the arylbromide of formula VII (13 mmol) in a mixture of tetrahydrofuran (10 ml) and toluene (30 ml) was treated at −78° C. with n-butyllithium (1.6 M in hexane, 7.8 ml) over 10 min while the temperature was kept below −70° C. Stirring was continued at −78° C. for 1 hour.

A solution of the dihydroisoxazole of formula VI (6.21 mmol) in toluene (70 ml) was treated at −78° C. with boron trifluoride etherate (12.4 mmol) followed by the addition over 10 minutes of the above aryllithium reagent using an insulated cannula keeping the temperature below −70° C. Thereafter the mixture was stirred at −78° C. for 30 minutes. After total 2 hours the reaction mixture quenched with a saturated aqueous solution of ammonium chloride and extracted three times with ethyl acetate. The combined organic layers were washed with brine, dried over sodium sulphate, and evaporated at reduced pressure. The crude product was purified by flash chromatography on silica gel using mixtures of heptane or cyclohexane and ethyl acetate as the eluent to yield the pure isoxazolidines of formula VIII.

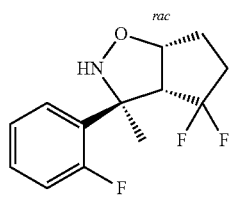 [SMILES: C[C@]1(c2ccccc2F)NO[C@@H]2CCC(F)(F)[C@@H]21]

Intermediate VIII-1: Starting from rac-(3aR,6aR)-4,4-difluoro-3-methyl-4,5,6,6a-tetrahydro-3aH-cyclopenta[d]isoxazole, the product rac-(3S,3aR,6aR)-4,4-difluoro-3-(2-fluoro-phenyl)-3-methyl-hexahydro-cyclopenta[d]isoxazole was obtained as a light yellow oil (73% yield). MS: m/z=258.1 [M+H]$^+$.

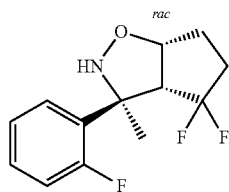 [SMILES: C[C@]1(c2ccccc2F)NO[C@@H]2CCC(F)(F)[C@@H]21]

Intermediate VIII-2: Starting from the 1:1-mixture of rac-(3aR,7aR)-4,4-difluoro-3-methyl-3a,4,5,6,7,7a-hexahydro-benzo[d]isoxazole and rac-(3 aR,7aR)-4-fluoro-3-methyl-3a,6,7,7a-tetrahydro-benzo[d]isoxazole, the product rac-(3S,3 aR,6aR)-4,4-difluoro-3-(2-fluoro-phenyl)-3-methyl-hexahydro-cyclopenta[d]isoxazole was obtained as a light yellow oil (29% yield). MS: m/z=272.1 [M+H]$^+$.

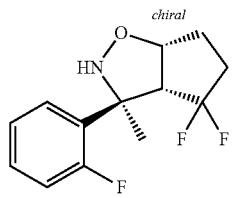 [SMILES: C[C@]1(c2ccccc2F)NO[C@@H]2CCC(F)(F)[C@@H]21]

Intermediates IX-1: The rac-(3S,3aR,6aR)-4,4-difluoro-3-(2-fluoro-phenyl)-3-methyl-hexahydro-cyclopenta[d]isoxazole was resolved by high-performance liquid chromatography (HPLC) on a chiral phase (Chiralpak AD) using a 90:10-mixture of n-heptane and ethanol as the eluent to give the (3R,3aS,6aS)-4,4-difluoro-3-(2-fluoro-phenyl)-3-methyl-hexahydro-cyclopenta[d]isoxazole (intermediate IXb-1) as the faster eluting enantiomer (30% yield) and the desired (3S,3aR,6aR)-4,4-difluoro-3-(2-fluoro-phenyl)-3-methyl-hexahydro-cyclopenta[d]isoxazole (intermediate IXa-1) as the slower eluting enantiomer (27% yield) both as light yellow oils.

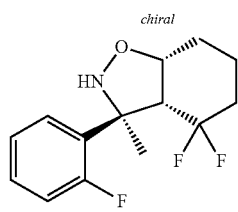 [SMILES: C[C@]1(c2ccccc2F)NO[C@@H]2CCCC(F)(F)[C@@H]21]

Intermediates IX-2: The rac-(3S,3aR,6aR)-4,4-difluoro-3-(2-fluoro-phenyl)-3-methyl-hexahydro-cyclopenta[d]isoxazole was resolved by high-performance liquid chromatography (HPLC) on a chiral phase (Chiralpak AD) using a 95:5-mixture of n-heptane and ethanol as the eluent to give the (3R,3aS,6aS)-4,4-difluoro-3-(2-fluoro-phenyl)-3-methyl-hexahydro-cyclopenta[d]isoxazole (intermediate IXb-2) as the faster eluting enantiomer (11% yield) and the desired (3S,3aR,6aR)-4,4-difluoro-3-(2-fluoro-phenyl)-3-methyl-hexahydro-cyclopenta[d]isoxazole (intermediate IXa-2) as the slower eluting enantiomer (22% yield).

General Procedure D: Synthesis of the Intermediate Aminoalcohols X

To a solution of the isoxazolidine of formula IX (1.52 mmol) in ethanol (8 ml) was added palladium (10% on carbon, 81 mg) and ammonium formate (767 mg) and stirring of the mixture was continued at 22° C. for 2.5 hours. Thereafter the suspension was filtered, the filtrate evaporated and the residue was partitioned between ethyl acetate and a saturated aqueous solution of sodium bicarbonate. The organic layer was dried over sodium sulphate, evaporated at reduced pressure to afford the pure aminoalcohol of formula X.

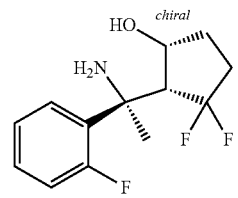 [SMILES: C[C@@](N)(c1ccccc1F)[C@@H]1[C@H](O)CCC1(F)F]

Intermediate Xa-1: Starting from (3S,3aR,6aR)-4,4-difluoro-3-(2-fluoro-phenyl)-3-methyl-hexahydro-cyclopenta[d]isoxazole (intermediate IXa-1), the product (1R,2R)-2-[(S)-1-amino-1-(2-fluoro-phenyl)-ethyl]-3,3-difluoro-cyclopentanol was obtained as a white crystalline solid (98% yield). MS: m/z=260.1 [M+H]$^+$.

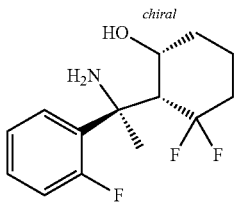 [SMILES: C[C@@](N)(c1ccccc1F)[C@@H]1[C@H](O)CCCC1(F)F]

Intermediate Xa-2: Starting from (3S,3aR,6aR)-4,4-difluoro-3-(2-fluoro-phenyl)-3-methyl-hexahydro-cyclopenta[d]isoxazole (intermediate IXa-2), the product (1R,2R)-2-[(S)-1-mino-1-(2-fluoro-phenyl)-ethyl]-3,3-difluoro-cyclohexanol was obtained as a white solid (98% yield). MS: m/z=274.1 [M+H]⁺.

General Procedure E: Synthesis of the Intermediate Oxazines XI

A solution of the aminoalcohol of formula X (1.4 mmol) in ethanol (7.5 ml) was treated at room temperature with a solution of cyanogen bromide (5M in acetonitrile; 2.85 mmol). The reaction mixture was heated at 85° C. in a sealed tube for 3-6 hours. In order to complete the reaction 1.4 mml of cyanogen bromide were added. After overall 22 hours the solvent was removed at reduced pressure and the residue partitioned between ethyl acetate and a saturated aqueous solution of sodium carbonate. The organic layer was separated, dried over sodium sulphate and evaporated at reduced pressure. The crude product was purified by flash chromatography on silica-NH₂ gel using mixtures of heptane or cyclohexane and ethyl acetate as the eluent to yield the pure isoxazolidines of formula XI.

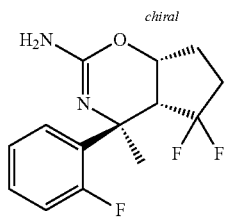 [SMILES: C[C@]1(c2ccccc2F)N=C(N)O[C@@H]2CCC(F)(F)[C@@H]21]

Intermediate XIa-1: Starting from (1R,2R)-2-[(S)-1-amino-1-(2-fluoro-phenyl)-ethyl]-3,3-difluoro-cyclopentanol, the product (4S,4aR,7aR)-5,5-difluoro-4-(2-fluoro-phenyl)-4-methyl-4,4a,5,6,7,7a-hexahydro-cyclopenta[e][1,3]oxazin-2-ylamine was obtained as a white foam (80% yield). MS: m/z=285.1 [M+H]⁺.

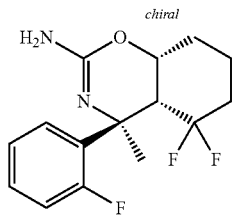 [SMILES: C[C@]1(c2ccccc2F)N=C(N)O[C@@H]2CCCC(F)(F)[C@@H]21]

Intermediate XIa-2: Starting from (1R,2R)-2-[(S)-1-mino-1-(2-fluoro-phenyl)-ethyl]-3,3-difluoro-cyclohexanol, the product (4S,4aR,8aR)-5,5-difluoro-4-(2-fluoro-phenyl)-4-methyl-4a,5,6,7,8,8a-hexahydro-4H-benzo[e][1,3]oxazin-2-ylamine was obtained as an amorphous white material (67% yield). MS: m/z=299.1 [M+H]⁺.

General Procedure F: Synthesis of the Intermediate Nitro-Oxazines XII

The oxazine of formula XI (0.1 mmol) was added portionwise to concentrated sulfuric acid (2 ml) at 22° C. The solution obtained was cooled to 0° C. and treated with red fuming nitric acid (0.058 ml) and stirring was continued at 0° C. for 2 hours. For the workup, the reaction mixture was slowly added to crushed ice and the pH was adjusted to 10 using a saturated solution of sodium carbonate. The aqueous layer was extracted with ethyl acetate, the organic layer was dried over sodium sulphate and evaporated to afford the pure nitro-oxazine of formula XII. Alternatively, the crude product was purified by flash chromatography on silica-NH₂ gel using mixtures of heptane or cyclohexane and ethyl acetate as the eluent to yield the pure nitro-oxazines of formula XII.

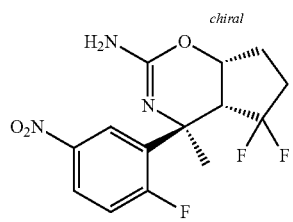 [SMILES: C[C@]1(c2cc([N+](=O)[O-])ccc2F)N=C(N)O[C@@H]2CCC(F)(F)[C@@H]21]

Intermediate XIIa-1: Starting from (4S,4aR,7aR)-5,5-difluoro-4-(2-fluoro-phenyl)-4-methyl-4,4a,5,6,7,7a-hexahydro-cyclopenta[e][1,3]oxazin-2-ylamine, the product (4S,4aR,7aR)-5,5-difluoro-4-(2-fluoro-5-nitro-phenyl)-4-methyl-4,4a,5,6,7,7a-hexahydro-cyclopenta[e][1,3]oxazin-2-ylamine was obtained as a white foam (87% yield). MS: m/z=330.1 [M+H]⁺.

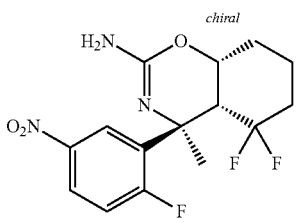 [SMILES: C[C@]1(c2cc([N+](=O)[O-])ccc2F)N=C(N)O[C@@H]2CCCC(F)(F)[C@@H]21]

Intermediate XIIa-2: Starting from (4S,4aR,8aR)-5,5-difluoro-4-(2-fluoro-phenyl)-4-methyl-4a,5,6,7,8,8a-hexahydro-4H-benzo[e][1,3]oxazin-2-ylamine, the product (4S,4aR,8aR)-5,5-difluoro-4-(2-fluoro-5-nitro-phenyl)-4-methyl-4a,5,6,7,8,8a-hexahydro-4H-benzo[e][1,3]oxazin-2-ylamine was obtained as a white solid (88% yield). MS: m/z=344.1 [M+H]⁺.

General Procedure G: Synthesis of the Intermediate Anilines XIII

A suspension of the nitro-oxazine of formula XII (0.68 mmol) in ethanol (4 ml) and triethylamine (0.095 ml) was hydrogenated at atmospheric pressure at 22° C. for 1.5 hours using palladium (10% on carbon; 72 mg) as the catalyst. For the workup, the reaction mixture was filtered and the filtrate evaporated to afford the pure anilines of formula XIII.

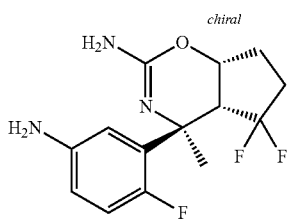

Intermediate XIIIa-1: Starting from (4S,4aR,7aR)-5,5-difluoro-4-(2-fluoro-5-nitro-phenyl)-4-methyl-4,4a,5,6,7,7a-hexahydro-cyclopenta[e][1,3]oxazin-2-ylamine, the product (4S,4aR,7aR)-4-(5-amino-2-fluoro-phenyl)-5,5-difluoro-4-methyl-4,4a,5,6,7,7a-hexahydro-cyclopenta[e][1,3]oxazin-2-ylamine was obtained as a white foam (97% yield). MS: m/z=300.1 [M+H]$^+$.

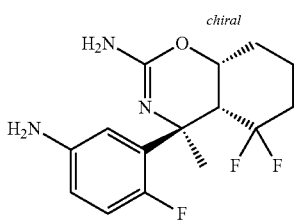

Intermediate XIIIa-2: Starting from (4S,4aR,8aR)-5,5-difluoro-4-(2-fluoro-5-nitro-phenyl)-4-methyl-4a,5,6,7,8,8a-hexahydro-4H-benzo[e][1,3]oxazin-2-ylamine, the product (4S,4aR,8aR)-4-(5-amino-2-fluoro-phenyl)-5,5-difluoro-4-methyl-4a,5,6,7,8,8a-hexahydro-4H-benzo[e][1,3]oxazin-2-ylamine was obtained as a white solid (75% yield). MS: m/z=314.0 [M+H]$^+$.

General Procedure Q for the Synthesis of the Final Amides I

A solution of acid XIV (95.8 μmol) in methanol (720 μl) was cooled to 0° C. 4-(4,6-dimethoxy-1,3,5-triazin-2-yl)-4-methylmorpholinium chloride (125 μmol) was added. After 5 minutes a solution of the aniline of formula XIII (95.8 μmol) in methanol (240 μl) was added dropwise. The mixture was stirred at 0° C. for 1 hour, then at room temperature overnight. For the workup, the solvent was removed at reduced pressure, then the residue treated with a saturated solution of sodium bicarbonate. The remaining solid was filtered, washed with water and dried at reduced pressure. The crude product was purified on silica-NH$_2$ gel using mixtures of heptane and ethyl acetate as the eluent to yield the pure final amides of formula I. Alternatively, the crude product was purified on HPLC using a gradient of water and acetonitrile (+0.1% of triethylamine) as the eluent.

The following examples were prepared according to general procedure Q.

EXAMPLE 1

5-But-2-ynyloxy-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-5,5-difluoro-4-methyl-4,4a,5,6,7,7a-hexahydro-cyclopenta[e][1,3]oxazin-2-ylamine (intermediate XIIIa-1) and 5-but-2-ynyloxy-pyrazine-2-carboxylic acid (CAS 1221447-98-8[14]) following procedure Q yielded the title compound as an amorphous colorless material (34% yield). MS: m/z=474.2 [M+H]$^+$.

EXAMPLE 2

5-Cyano-pyridine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-5,5-difluoro-4-methyl-4,4a,5,6,7,7a-hexahydro-cyclopenta[e][1,3]oxazin-2-ylamine (intermediate XIIIa-1) and 5-cyano-pyridine-2-carboxylic acid following procedure Q yielded the title compound as a white powder (82% yield). MS: m/z=430.4 [M+H]$^+$.

EXAMPLE 3

5-Chloro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-5,5-difluoro-4-methyl-4,4a,5,6,7,7a-hexahydro-cyclopenta[e][1,3]oxazin-2-ylamine (intermediate XIIIa-1) and 5-chloro-pyridine-2-carboxylic acid following procedure Q yielded the title compound as an amorphous colorless material (69% yield). MS: m/z=439.2 [M+H]$^+$.

EXAMPLE 4

5-(1,1-Difluoro-ethyl)-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-5,5-difluoro-4-methyl-4,4a,5,6,7,7a-hexahydro-cyclopenta[e][1,3]oxazin-2-ylamine (intermediate XIIIa-1) and 5-(1,1-difluoro-ethyl)-pyrazine-2-carboxylic acid (CAS 1262803-63-315) following procedure Q yielded the title compound as a white solid (52% yield). MS: m/z=470.3 [M+H]$^+$.

EXAMPLE 5

5-Fluoromethyl-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-5,5-difluoro-4-methyl-4,4a,5,6,7,7a-hexahydro-cyclopenta[e][1,3]oxazin-2-ylamine (intermediate XIIIa-1) and 5-fluoromethyl-pyrazine-2-carboxylic acid (CAS 1262803-

66-6) following procedure Q yielded the title compound as a white solid (75% yield). MS: m/z=438.2 [M+H]⁺.

EXAMPLE 6

5-Cyano-pyrazine-2-carboxylic acid [3-((4S,4aR, 7aR)-2-amino-5,5-difluoro-4-methyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-5,5-difluoro-4-methyl-4,4a,5,6,7,7a-hexahydro-cyclopenta[e][1,3]oxazin-2-ylamine (intermediate XIIIa-1) and 5-cyano-pyrazine-2-carboxylic acid (CAS 1211533-09-3) following procedure Q yielded the title compound as a light yellow solid (28% yield). MS: m/z=431.3 [M+H]⁺.

EXAMPLE 7

5-Chloro-pyridine-2-carboxylic acid [3-((4S,4aR, 8aR)-2-amino-5,5-difluoro-4-methyl-4a,5,6,7,8,8a-hexahydro-4H-benzo[e][1,3]oxazin-4-yl)-4-fluoro-phenyl]-amide The coupling of (4S,4aR,8aR)-4-(5-amino-2-fluoro-phenyl)-5,5-difluoro-4-methyl-4a,5,6,7,8,8a-hexahydro-4H-benzo[e][1,3]oxazin-2-ylamine (intermediate XIIIa-2) and 5-chloro-pyridine-2-carboxylic acid following procedure Q yielded the title compound as a white solid (85% yield). MS: m/z=453.1 [M+H]⁺.

EXAMPLE 8

5-Cyano-pyridine-2-carboxylic acid [3-((4S,4aR, 8aR)-2-amino-5,5-difluoro-4-methyl-4a,5,6,7,8,8a-hexahydro-4H-benzo[e][1,3]oxazin-4-yl)-4-fluoro-phenyl]-amide The coupling of (4S,4aR,8aR)-4-(5-amino-2-fluoro-phenyl)-5,5-difluoro-4-methyl-4a,5,6,7,8,8a-hexahydro-4H-benzo[e][1,3]oxazin-2-ylamine (intermediate XIIIa-2) and 5-cyano-pyridine-2-carboxylic acid following procedure Q yielded the title compound as a white solid (72% yield). MS: m/z=444.3 [M+H]⁺.

EXAMPLE 9

5-Chloro-thiophene-2-carboxylic acid [3-((4S,4aR, 8aR)-2-amino-5,5-difluoro-4-methyl-4a,5,6,7,8,8a-hexahydro-4H-benzo[e][1,3]oxazin-4-yl)-4-fluoro-phenyl]-amide The coupling of (4S,4aR,8aR)-4-(5-amino-2-fluoro-phenyl)-5,5-difluoro-4-methyl-4a,5,6,7,8,8a-hexahydro-4H-benzo[e][1,3]oxazin-2-ylamine (intermediate XIIIa-2) and 5-chloro-thiophene-2-carboxylic acid (CAS 24065-33-6) following procedure Q yielded the title compound as a white solid (72% yield). MS: m/z=458.3 [M+H]⁺.

[1] Hardy et al., The amyloid hypothesis of Alzheimer's disease: progress and problems on the road to therapeutics, *Science*. 2002 Jul. 19; 297(5580):353-6
[2] Selkoe, Cell biology of the amyloid beta-protein precursor and the mechanism of Alzheimer's disease, *Annu Rev Cell Biol*. 1994; 10:373-403
[3] Vassar et al., Beta-secretase cleavage of Alzheimer's amyloid precursor protein by the transmembrane aspartic protease BACE, *Science*. 1999 Oct. 22; 286(5440): 735
[4] Luo et al., Mice deficient in BACE1, the Alzheimer's beta-secretase, have normal phenotype and abolished beta-amyloid generation, *Nat Neurosci*. 2001 March; 4(3):231-2
[5] Roberds et al., BACE knockout mice are healthy despite lacking the primary beta-secretase activity in brain: implications for Alzheimer's disease therapeutics, *Hum Mol Genet*. 2001 Jun. 1; 10(12):1317-24
[6] McConlogue et al., Partial reduction of BACE1 has dramatic effects on Alzheimer plaque and synaptic pathology in APP Transgenic Mice. *J Biol Chem*. 2007 Sep. 7, 282(36): 26326
[7] WO 2011071135
[8] Biochem. Pharmacol. (1973) 22:3099
[9] Compendium of Chemical Terminology, 2nd, A. D. McNaught & A. Wilkinson (Eds). Blackwell Scientific Publications, Oxford (1997)
[10] Brockhaus et al., NeuroReport 9, 1481-1486; 1998
[11] R. L. Walsky and R. S. Obach, Drug Metabolism and Disposition 32: 647-660, 2004. and S. Fowler and H. Zhang, The AAPS Journal, Vol. 10, No. 2, 410-424, 2008
[12] Guo L, Guthrie H, Automated electrophysiology in the preclinical evaluation of drugs for potential QT prolongation. *Journal of Pharmacological & Toxicological Methods*, (2005) 52(1):123-35
[13] C. M. Dieckhaus et al. in *Chem. Res. Toxicol.* 2005, 18, 630-638
[14] WO2010047372
[15] WO2011009898

The invention claimed is:
1. A compound of formula I,

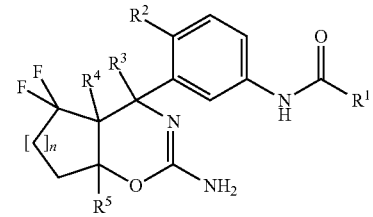

wherein:
$R^1$ is selected from the group consisting of
  i) aryl,
  ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{2-6}$-alkyl,
  iii) heteroaryl, and
  iv) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;
$R^2$ is selected from the group consisting of
  i) hydrogen,
  ii) $C_{1-6}$-alkyl, and
  iii) halogen;
$R^3$ is selected from the group consisting of
  i) $C_{1-6}$-alkyl, and
  ii) halogen-$C_{1-6}$-alkyl;
$R^4$ is selected from the group consisting of
  i) hydrogen, and
  ii) $C_{1-6}$-alkyl, and R⁵ is selected from the group consisting of
i) hydrogen, and
ii) $C_{1-6}$-alkyl; and
n is 1 or 2;
or pharmaceutically acceptable salts thereof.

2. The compound of formula I according to claim 1, wherein R¹ is heteroaryl substituted by 1-2 substituents individually selected from cyano, halogen, halogen-$C_{1-6}$-alkyl and $C_{2-6}$-alkynyl-$C_{1-6}$-alkoxy.

3. The compound of formula I according to claim 1, wherein R¹ is selected from
i) pyridinyl substituted by 1-2 substituents individually selected from cyano and halogen,
ii) pyrazinyl substituted by 1-2 substituents individually selected from cyano, halogen-$C_{1-6}$alkyl and $C_{2-6}$-alkynyl-$C_{1-6}$-alkoxy, and
iii) thiophenyl substituted by 1-2 halogen.

4. The compound of formula I according to claim 1, wherein R¹ is 5-but-2-ynyloxy-pyrazin-2-yl, 5-cyano-pyridin-2-yl, 5-chloro-pyridin-2-yl, 5-fluoromethyl-pyrazin-2-yl, 5-cyano-pyrazin-2-yl, 5-chloro-pyridin-2-yl, 5-cyano-pyridin-2-yl, 5-chloro-thiophen-2-yl or 5-(1,1-difluoro-ethyl)-pyrazin-2-yl.

5. The compound of formula I according to claim 1, wherein R² is halogen.

6. The compound of formula I according to claim 1, wherein R² is F.

7. The compound of formula I according to claim 1, wherein R³ is $C_{1-6}$-alkyl.

8. The compound of formula I according to claim 1, wherein R³ is methyl.

9. The compound of formula I according to claim 1, wherein R⁴ is hydrogen.

10. The compound of formula I according to claim 1, wherein R⁵ is hydrogen.

11. The compound of formula I according to claim 1, wherein n is 1.

12. The compound of formula I according to claim 1, wherein n is 2.

13. The compound of formula I according to claim 1, selected from the group consisting of:
5-But-2-ynyloxy-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-henyl]-amide,
5-Fluoromethyl-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide,
5-Cyano-pyridine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide,
5-Chloro-pyridine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide,
5-Cyano-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl-amide,
5-Chloro-pyridine-2-carboxylic acid [3-((4S,4aR,8aR)-2-amino-5,5-difluoro-4-methyl-4a,5,6,7,8,8a-hexahydro-4H-benzo[e][1,3]oxazin-4-yl)-4-fluoro-phenyl]-amide,
5-Cyano-pyridine-2-carboxylic acid [3-((4S,4aR,8aR)-2-amino-5,5-difluoro-4-methyl-4a,5,6,7,8,8a-hexahydro-4H-benzo[e][1,3]oxazin-4-yl)-4-fluoro-phenyl]-amide,
5-Chloro-thiophene-2-carboxylic acid [344S,4aR,8aR)-2-amino-5,5-difluoro-4-methyl-4a,5,6,7,8,8a-hexahydro-4H-benzo[e][1,3]oxazin-4-yl)-4-fluoro-phenyl]-amide, and
5-(1,1-Difluoro-ethyl)-pyrazine-2-carboxylic acid [3-((4S,4aR,7aR)-2-amino-5,5-difluoro-4-methyl-4,4a,5,6,7,7a-hexahydro-cyclopenta[e][1,3]oxazin-4-yl)-4-fluoro-phenyl]-amide,
or a pharmaceutical acceptable salt thereof.

14. A process for preparing a compound of formula I according to claim 1, comprising the step of reacting a compound of formula I' with a compound of formula XIV:

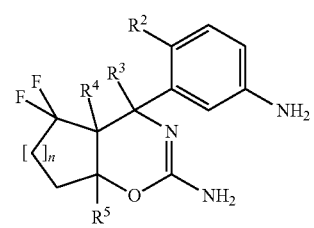

I'

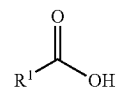

XIV wherein n, R¹, R², R³, R⁴, R⁵ are as defined in claim 1.

15. A pharmaceutical composition comprising a compound of formula I according to claim 1 and a pharmaceutically acceptable carrier and/or a pharmaceutically acceptable auxiliary substance.

16. A method for the treatment of Alzheimer's Disease, comprising the step of administering a therapeutically effective amount of a compound according to claim 1 to a human being or animal in need thereof.

* * * * *